United States Patent [19]

Allan

[11] Patent Number: 5,906,979
[45] Date of Patent: May 25, 1999

[54] COMPOSITIONS AND METHODS FOR TREATING METABOLIC DISEASES CHARACTERIZED BY HYPERANDROGENISM AND/OR ANOVULATION AND/OR INFERTILITY

[75] Inventor: Geoffrey Allan, Richmond, Va.

[73] Assignee: Insmed Pharmaceuticals, Inc., Richmond, Va.

[21] Appl. No.: 09/014,398

[22] Filed: Jan. 27, 1998

[51] Int. Cl.⁶ ........................................... A61K 31/70
[52] U.S. Cl. ................................. 514/25; 514/824
[58] Field of Search ........................ 514/25, 824

[56] References Cited

U.S. PATENT DOCUMENTS

| | | | |
|---|---|---|---|
| 3,773,919 | 11/1973 | Boswell et al. | 424/19 |
| 4,485,045 | 11/1984 | Regen | 260/403 |
| 4,544,545 | 10/1985 | Ryan et al. | 424/1.1 |
| 5,550,166 | 8/1996 | Ostlund et al. | 514/715 |

FOREIGN PATENT DOCUMENTS

| | | |
|---|---|---|
| 0 036 676 | 9/1981 | European Pat. Off. . |
| 0 052 322 | 5/1982 | European Pat. Off. . |
| 0 058 481 | 8/1982 | European Pat. Off. . |
| 0 088 046 | 9/1983 | European Pat. Off. . |
| 0 102 324 | 3/1984 | European Pat. Off. . |
| 0 133 988 | 3/1985 | European Pat. Off. . |
| 0 142 641 | 5/1985 | European Pat. Off. . |
| 0143 949 | 6/1985 | European Pat. Off. . |
| 3218121 | 11/1983 | Germany . |
| 58-118008 | 7/1983 | Japan . |

OTHER PUBLICATIONS

Carmina, E. et al., "Does ethnicity influence the prevalence of adrenal hyperandrogensim and insulin resistance in polycystic ovary syndrome?" *Am. J. Obstetrics and Gynecology* 167:1807–1812 (1992).

Ciaraldi, T. et al., "Cellular Mechanisms of Insulin Resistance in Polycystic Ovarian Syndrom," *J. Clin. Endocrinology and Metabolism* 75:577–583 (1992).

Dunaif, A. et al., "Excessive Insulin Receptor Serine Phosphorylation in Cultured Fibroblasts and in Skeletal Muscle," *J. Clin. Invest.* 96:801–810 (1995).

Dunaif, A. et al., "The Insulin–Sensitizing Agent Troglitazone Improves Metabolic and Reproductive Abnormalities in the Polycystic Ovary Syndrome," *J. Clin. Endocrinology and Metabolism* 81:3299–3306 (1996).

Eppstein, D. et al., "Biological activity of liposome–encapsulated murine interferon γ is mediated by a cell membrane receptor," *Proc. Natl. Acad. Sci. USA* 82:3688–3692 (1985).

Hwang, K. et al., "Hepatic uptake and degradation of unilamellar sphingomyelin/cholesterol liposomes: A kinetic study," *Proc. Natl. Acad. Sci. USA* 77:4030–4034 (1980).

Jakubowicz, D. and J. Nestler, "17α–Hydroxyprogesterone Responses to Leuprolide and Serum Androgens in Obese Women with and without Polycystic Ovary Syndrome after Dietary Weight Loss," *J. Clin. Endocrinology and Metabolism* 82: 556–560 (Feb. 1997).

Langer, R. et al., "Biocompatibility of polymeric delivery systems for macromolecules," *J. Biomed. Materials Res.* 15:267–277 (1981).

Langer, R., "Controlled release of macromolecules," *Chemtech* 12:98–105 (1982).

Nestler, J. and D. Jakubowicz, "Decreases In Ovarian Cytochrome P450c17α Activity And Serum Free Testosterone After Reduction Of Insulin Secretion In Polycystic Ovary Syndrome," *New England J. Med.* 335:617–623 (1996).

Sidman, K. et al., "Controlled Release of Macromolecules and Pharmaceuticals from Synthetic Polypeptides Based on Glutamic Acid," *Biopolymers* 22:547–556 (1983).

Dialog File 351, Derwent WPI English language abstract for EP 0 052 322. (1982).

Dialog File 351, Derwent WPI English language abstract for JP 58–118008. (JP 60–007934) (1983).

Dialog File 351, Derwent WPI English language abstract for EP 0 088 046. (1983).

Dialog File 351, Derwent WPI English language abstract for DE 3218121. (1983).

Dialog File 351, Derwent WPI English language abstract for EP 0 102 324. (1984).

Dialog File 351, Derwent WPI English language abstract for EP 0 133 988. (1985).

Dialog File 351, Derwent WPI English language abstract for EP 0 142 641. (AU 8433327) (1985).

*Primary Examiner*—Kimberly Jordan
*Attorney, Agent, or Firm*—Sterne, Kessler, Goldstein & Fox P.L.L.C.

[57] ABSTRACT

This invention relates to compositions and methods for decreasing the level of serum insulin, triglycerides, cholesterol, and/or free and total testosterone, and/or improving ovulation, and/or increasing progesterone and/or sex hormone binding globulin in mammals. This invention also relates to compositions and methods for treating metabolic diseases characterized by hyperinsulinemia, hyperandrogenism, hyperlipidemia and/or anovulation, such as polycystic ovary syndrome.

36 Claims, 6 Drawing Sheets

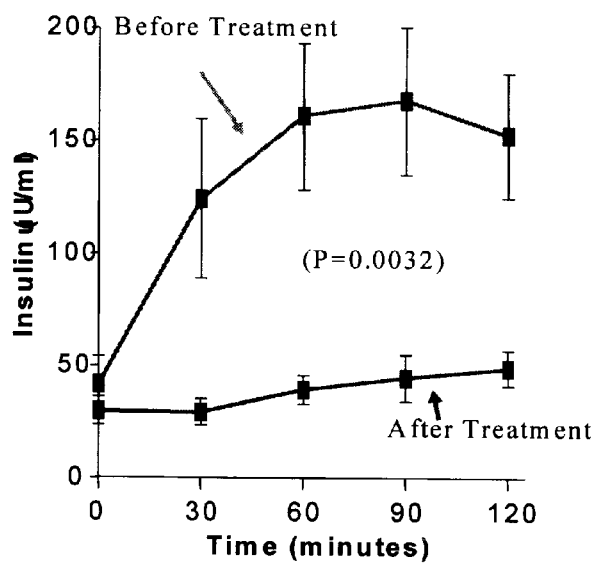
Figure 1. Administration of INS-1 for up to 8 weeks in 14 women diagnosed with PCOS resulted in a significant 72% decrease in insulin response (area under the curve) to a 75 gram glucose load.

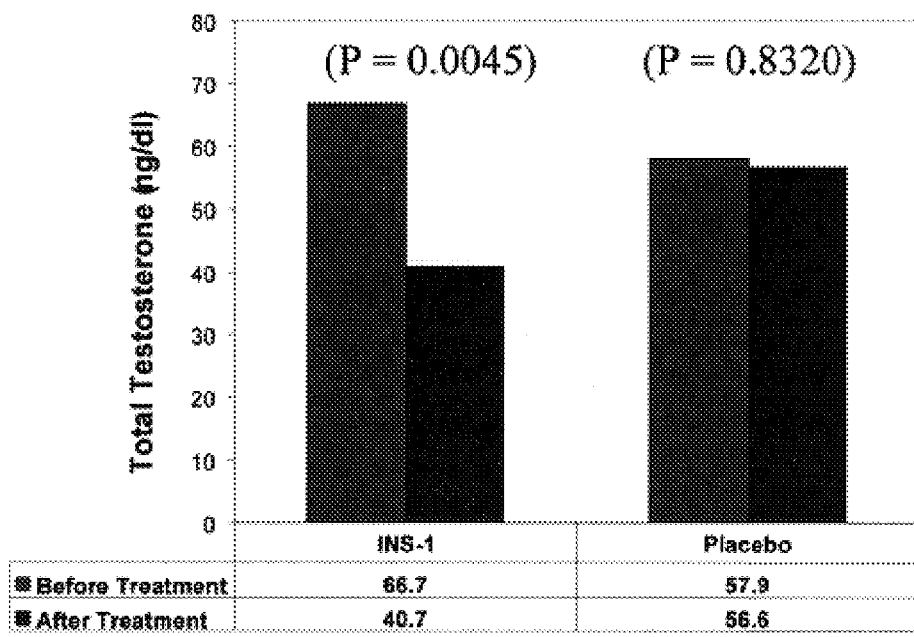
Figure 2. Administration of INS-1 for up to 8 weeks in 14 women diagnosed with PCOS resulted in a significant 39% decrease in total testosterone. No difference was observed in the 15 women receiving placebo.

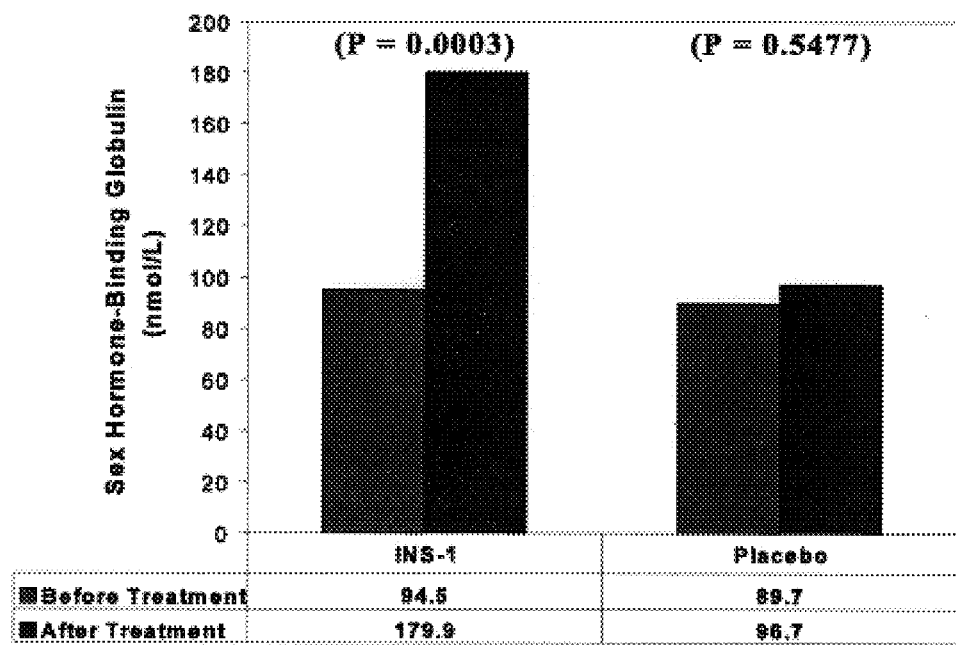
Figure 3.  Administration of INS-1 for up to 8 weeks in 14 women diagnosed with PCOS resulted in a significant 90% increase in sex hormone binding globulin. No difference was observed in the 15 women receiving placebo.

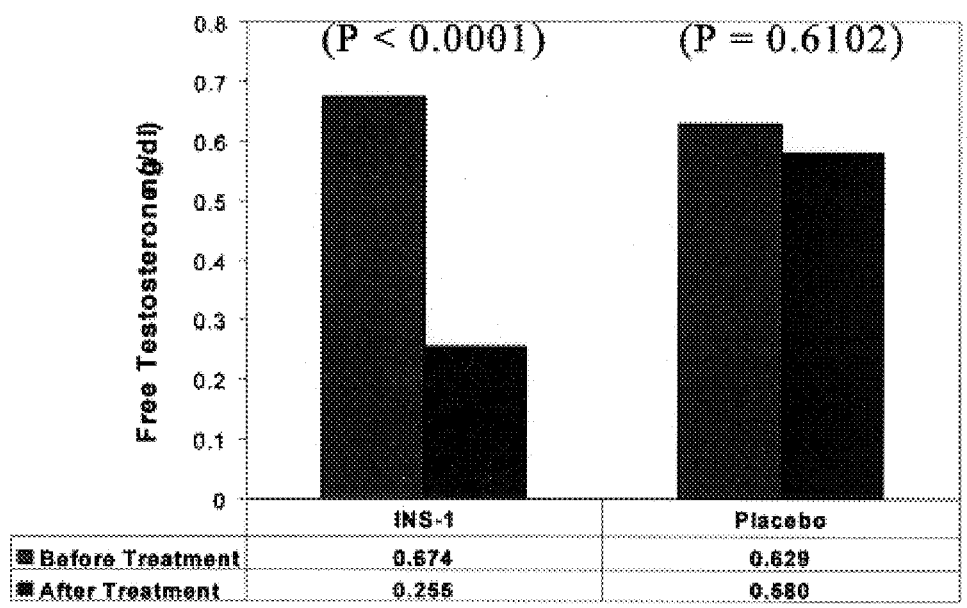
Figure 4.   Administration of INS-1 for up to 8 weeks in 14 women diagnosed with PCOS resulted in a significant 62% decrease in free testosterone. No difference was observed in the 15 women receiving placebo.

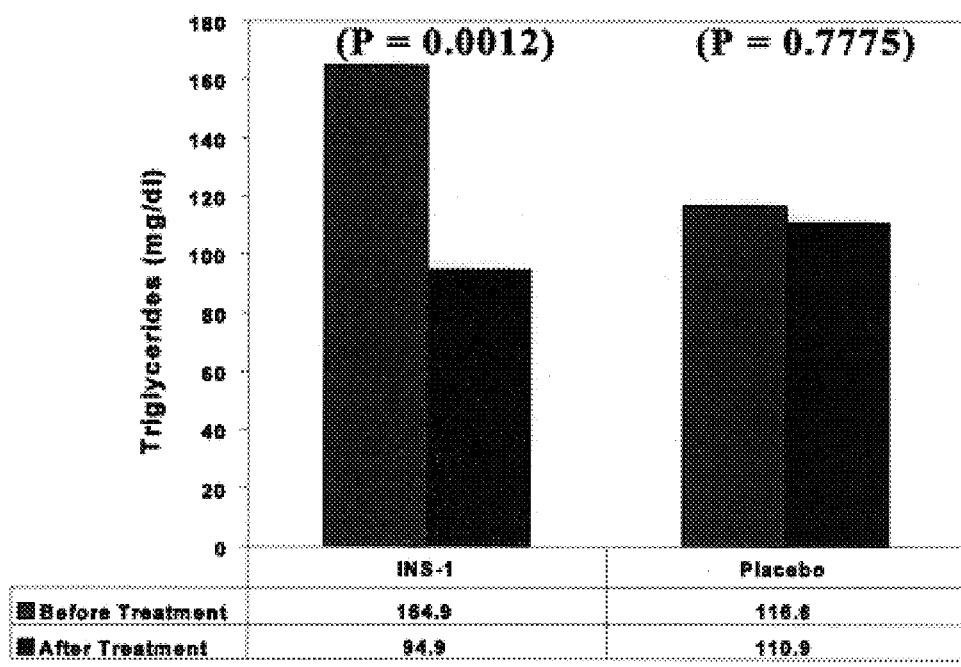
Figure 5.    Administration of INS-1 for up to 8 weeks in 14 women diagnosed with PCOS resulted in a significant 42% decrease in triglycerides. No difference was observed in the 15 women receiving placebo.

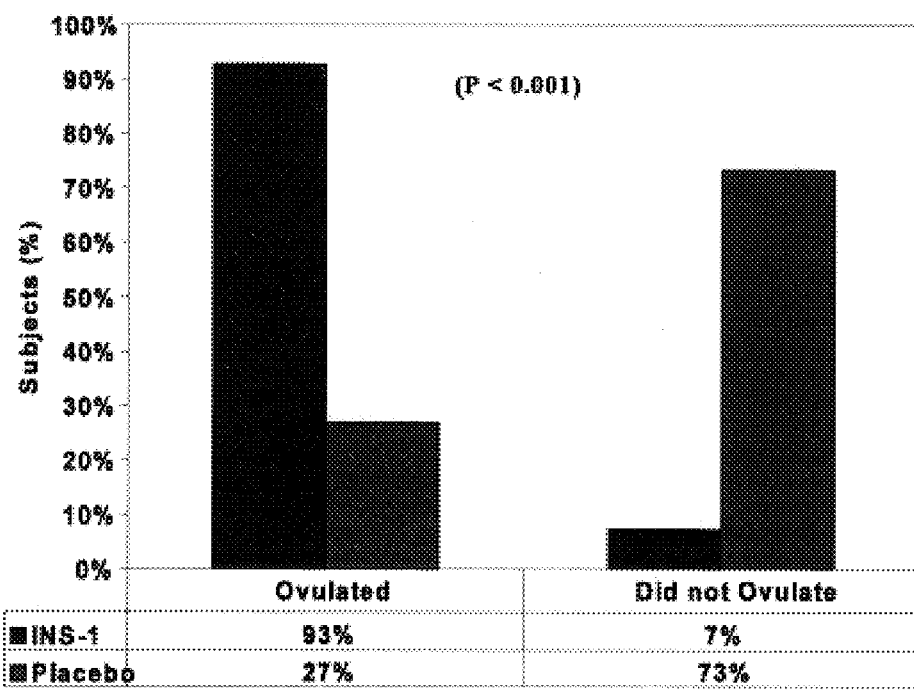
Figure 6. Administration of INS-1 for up to 8 weeks in 14 women diagnosed with PCOS resulted in a significant 93% ovulation rate compared to a 27% ovulation rate in the 15 women who received placebo.

COMPOSITIONS AND METHODS FOR TREATING METABOLIC DISEASES CHARACTERIZED BY HYPERANDROGENISM AND/OR ANOVULATION AND/OR INFERTILITY

FIELD OF THE INVENTION

This invention relates to compositions and methods for decreasing serum insulin, triglycerides, cholesterol, free and total testosterone levels and/or improving ovulation and/or increasing progesterone and/or sex hormone binding globulin in mammals. This invention also relates to compositions and methods for treating metabolic diseases characterized by hyperinsulinemia, hyperandrogenism, hyperlipidemia and/or anovulation, such as polycystic ovary syndrome (PCOS).

BACKGROUND OF THE INVENTION

Female mammals with chronic anovulation who experience withdrawal bleeding after progesterone administration are said to be in a state of "estrus" due to the acyclic production of estrogen, largely estrone, by extraglandular aromatization of circulating androstendione. The most common terms for this disorder are "polycystic ovary syndrome" (PCOS) and "polycystic ovarian disease" (PCOD).

PCOS is characterized by infertility, hirsutism, obesity, particularly central obesity, which is characterized by an increased waist/hip ratio), acne and/or amenorrhea or oligomenorrhea. When spontaneous uterine bleeding occurs in patients with PCOS; it is unpredictable with respect to time of onset, duration, and amount, and on occasion the bleeding can be severe. The dysfunctional uterine bleeding is usually due to estrogen breakthrough.

PCOS, which may be transmitted as an autosomal dominant or X-linked trait, was originally described as characterized by enlarged, polycystic ovaries, but the syndrome and its accompanying endocrine abnormalities are now known to be associated with a variety of pathologic findings in the ovaries, only some of which result in enlargement of the ovaries and none of which are pathognomonic. The most common finding is a white, smooth, sclerotic ovary with a thickened capsule, multiple follicular cysts in various stages of atresia, a hyperplastic theca and stroma, and rare or absent corpora albicans. Other ovaries have hyperthecosis in which the ovarian stroma is hyperplastic and may contain lipid-laden luteal cells. Thus, the diagnosis of PCOS is a clinical one, based on the coexistence of chronic anovulation and varying degrees of androgen excess.

In most women with PCOS, menarche occurs at the expected time, but uterine bleeding is unpredictable in onset, duration and amount. Amenorrhea ensues after a variable time, although primary amenorrhea occurs in some women. Signs of androgen excess, such as hirsutism, usually become evident around the time of menarche.

One proposed mechanism for the initiation and perpetuation of chronic anovulation suggests that PCOS originates as an exaggerated adrenarche in obese girls. The combination of elevated adrenal androgens and obesity would result in increased formation of extraglandular estrogen and lead to an acyclic positive feedback on LH secretion and negative feedback on FSH secretion so that characteristic LH/FSH ratios in plasma would be greater than 2. The increased LH levels could then lead to hyperplasia of the ovarian stroma and theca cells and increased androgen production, which in turn would provide more substrate for peripheral aromatization and perpetuate the chronic anovulation. In the advanced state of PCOS, the ovary is the major site of androgen production, but the adrenal may continue to secrete excess androgen as well. The greater the obesity, the more this sequence will be perpetuated because adipose (fat) tissue aromatizes androgens to estrogens, which in turn exaggerates inappropriate LH release by positive feedback.

Thus, the fundamental defect in PCOS is viewed as one of inappropriate signals to the hypothalamus and the pituitary. In fact, the hypothalamus-pituitary axis responds appropriately to high levels of estrogen, and ovulation can be induced with anti-estrogens such as clomiphene citrate. Increased levels of plasma endorphins and inhibin contribute to the perpetuation of this defect.

The concept that the fundamental defect in PCOS is one of inappropriate signals is supported by the empirical evidence from the ovaries. More specifically, ovarian follicles from women with PCOS have low aromatase activity, but normal aromatase can be induced when the follicles are treated with FSH. Thus, the anovulation is not due to an intrinsic abnormality in the ovary, but rather results from FSH deficiency and LH excess.

Conventional treatment of PCOS may be directed at interrupting this self-perpetuating cycle. Such treatments include: wedge resection or oral contraceptives, to decrease ovarian androgen secretion; weight loss, to decrease peripheral estrogen formation; or treatment with clomiphene, human menopausal gonadotropin (hMY), or LHRH (gonadorelin), to enhance FSH secretion.

During the past decade, it has become apparent that many women suffering from PCOS are characterized by hyperinsulinemia. Both obese and non-obese women with PCOS are more hyperinsulinemic than age and weight matched normal women (Ciraldi et al., *J Clin. Endocrinol. Metab.* 75:577–583 (1992); Dunaif et al., *J Clin. Invest.* 96:801–810 (1995)). Hyperinsulinemia is a feature of PCOS not only in the United States, but also in other societies.

For example, studies conducted in the United States, Japan and Italy demonstrated that women with PCOS all manifested hyperinsulinemia when compared to their respective normal counterparts (Carmina et al, *J Obstet. Gynecol.* 167:1807–1812 (1992)). This common finding across multiple ethnic groups suggests that hyperinsulinemia represents a fundamental feature of PCOS in many affected women.

More important, recent studies (Nestler et al., *New Engl. J Med.* 335:617–623 (1996); Jakubowicz et al, *J Clin. Endo. Metab.* (1997)(in press); Dunaif et al., *J Clin. Endo. Metab.* 81:3299–3306 (1996)) have demonstrated that excess androgen concentrations are decreased when hyperinsulinemia is reduced pharmacologically, with either metformin or troglitazone, or by dietary means.

All of these observations lead to the conclusion that correction of the underlying hyperinsulinemia may be an important target for clinical intervention in PCOS.

SUMMARY OF THE INVENTION

It has been found that certain isomers of inositol, namely D-chiro-inositol and derivatives and metabolites thereof and compounds containing D-chiro-inositol or a derivative or metabolite thereof, have significant effects on mammalian endocrinology and metabolism. More specifically, D-chiro-inositol and derivatives and metabolites thereof and compounds containing D-chiro-inositol or a derivative or metabolite thereof, when administered to subjects suffering from metabolic diseases characterized by hyperinsulinemia, hyperandrogenism, hyperlipidemia and/or anovulation, decrease serum insulin levels, decrease serum triglyceride levels, decrease serum cholesterol levels, decrease free and total testosterone levels, improve ovulation and/or increase progesterone and sex hormone binding globulin.

Accordingly, a first embodiment of the present invention is directed to a composition for decreasing serum insulin levels, decreasing serum triglyceride levels, decreasing serum cholesterol levels, decreasing free and total testosterone levels and/or improving ovulation and/or increasing progesterone and/or sex hormone binding globulin in mammals suffering from metabolic diseases characterized by hyperinsulinemia, hyperandrogenism, hyperlipidemia and/or anovulation, which comprises an effective amount of D-chiro-inositol, or a suitable derivative or metabolite thereof, or a compound containing D-chiro-inositol or a derivative or metabolite thereof, and an acceptable carrier.

A second embodiment of the present invention is directed to a method for decreasing serum insulin levels, decreasing serum triglyceride levels, decreasing serum cholesterol levels, decreasing free and total testosterone levels and/or improving ovulation and/or increasing progesterone and/or sex hormone binding globulin in mammals suffering from metabolic diseases characterized by hyperinsulinemia, hyperandrogenism, hyperlipidemia and/or anovulation, which comprises the step of administering to a mammal an effective amount of D-chiro-inositol, or a suitable derivative or metabolite thereof or a compound containing D-chiro-inositol or a derivative or metabolite thereof A third embodiment of the present invention is directed to a composition for treating mammalian metabolic diseases characterized by hyperinsulinemia, hyperandrogenism, hyperlipidemia and/or anovulation, such as polycystic ovary syndrome, which comprises an effective amount of D-chiro-inositol, or a suitable derivative or metabolite thereof or a compound containing D-chiro-inositol or a derivative or metabolite thereof, and an acceptable carrier.

A fourth embodiment of the present invention is directed to a method for treating mammalian metabolic diseases characterized by hyperinsulinemia, hyperandrogenism, hyperlipidemia and/or anovulation, such as polycystic ovary syndrome, which comprises the step of administering to a mammal in need thereof an effective amount of D-chiro-inositol, or a suitable derivative or metabolite thereof or a compound containing D-chiro-inositol or a derivative or metabolite thereof.

It is to be understood that both the foregoing general description and the following detailed description are exemplary and explanatory only and are intended to provide further explanation of the invention as claimed.

BRIEF DESCRIPTION OF THE FIGURES

FIG. 1 is a graph showing the 72% decrease in insulin response (area under the curve) to a 75 g glucose load in subject women following four to eight weeks of treatment with D-chiro-inositol.

FIG. 2 is a graph showing the 39% decrease in fasting total testosterone in subject women following four to eight weeks of treatment with D-chiro-inositol.

FIG. 3 is a graph showing the 90% increase in fasting sex hormone binding globulin in subject women following four to eight weeks of treatment with D-chiro-inositol.

FIG. 4 is a graph showing the 62% decrease in free testosterone (calculated) in subject women following four to eight weeks of treatment with D-chiro-inositol.

FIG. 5 is a graph showing the 42% decrease in triglycerides in subject women following four to eight weeks of treatment with D-chiro-inositol.

FIG. 6 is a graph showing the 93% ovulation rate in subject women following four to eight weeks of treatment with D-chiro-inositol.

DETAILED DESCRIPTION OF THE PREFERRED EMBODIMENTS

In a first preferred embodiment, the present invention is directed to compositions and methods for decreasing serum insulin levels, decreasing serum triglyceride levels, decreasing serum cholesterol levels, decreasing free and total testosterone levels and/or improving ovulation and/or increasing progesterone and/or sex hormone binding globulin in mammals suffering from metabolic diseases characterized by hyperinsulinemia, hyperandrogenism, hyperlipidemia and/or anovulation.

The inventive composition comprises an effective amount of D-chiro-inositol, or a suitable derivative or metabolite thereof, or a compound containing D-chiro-inositol or a derivative or metabolite thereof, and an acceptable carrier. Preferably, the inventive composition comprises an effective amount of D-chiro-inositol or a compound containing D-chiro-inositol.

The inventive method comprises the step of administering to a mammal in need thereof an effective amount of D-chiro-inositol, or a suitable derivative or metabolite thereof, or a compound containing D-chiro-inositol or a derivative or metabolite thereof. Preferably, the inventive method comprises the step of administering to a mammal in need thereof an effective amount of D-chiro-inositollor a compound containing D-chiro-inositol.

While the inventive composition preferably comprises D-chiro-inositol or a compound containing D-chiro-inositol, suitable derivatives and/or metabolites of D-chiro-inositol, or compounds containing derivatives or metabolites of D-chiro-inositol, may also be employed.

As used herein, a "suitable derivative or metabolite" of D-chiro-inositol is a compound based on or derived from the D-chiro-inositol moiety. Illustrative examples of suitable derivatives and metabolites of D-chiro-inositol include, but are not limited to, the following: D-chiro-inositol phosphates; D-chiro-inositol esters, preferably acetates; D-chiro-inositol ethers, preferably lower alkyl ethers; D-chiro-inositol acetals; and D-chiro-inositol ketals.

As used herein, a "compound containing D-chiro-inositol" is any compound that contains the D-chiro-inositol moiety. Illustrative examples of D-chiro-inositol containing compounds include, but are not limited to, the following: polysaccharides containing D-chiro-inositol and one or more additional sugars, such as glucose, galactose and mannose, or derivatives thereof, such as glucosamine, galactosamine and mannitol; D-chiro-inositol phospholipids; and complexes or chelates of D-chiro-inositol with one or more metal ions and the like.

The active agent in the inventive composition (i.e. D-chiro-inositol or a suitable derivative or metabolite thereof or a compound containing D-chiro-inositol, or a derivative or metabolite thereof) may be used alone or in admixture with one or more additional active agents. For example, a composition according to the first embodiment of the present invention may include D-chiro-inositol and a compound containing D-chiro-inositol in admixture.

As used herein, an "acceptable carrier" is a non-toxic solid, semisolid or liquid filler, diluent, encapsulating material or formulation auxiliary of any type known to those skilled in the art for use in pharmaceuticals.

When administered to a mammal, the inventive compositions may be administered orally, rectally, parenterally, intracistemally, intravaginally, intraperitoneally, topically (as by powders, ointments, drops or transdermal patch), bucally, or as an oral or nasal spray. Preferably, the inventive compositions are administered orally, for example in the form of a tablet or capsule.

As used herein, the term "parenteral" refers to modes of administration which include intravenous, intramuscular, intraperitoneal, intrastemal, subcutaneous and intraarticular injection and infusion.

The compositions of the present invention are also suitably administered by sustained-release systems. Suitable examples of sustained-release compositions include semipermeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman et al., Biopolymers 22:547–556 (1983)), poly (2-hydroxyethyl methacrylate) (Langer et al., *J Biomed. Mater. Res*. 15:167–277 (1981), and Langer, Chem. Tech. 12:98–105 (1982)), ethylene vinyl acetate (Langer et al.) or poly-D-(-)-3-hydroxybutyric acid (EP 133,988).

Sustained-release compositions also include liposomally entrapped compounds. Liposomes containing one or more of the compounds of the present invention may be prepared by methods knownper se: DE 3,218,121; Epstein et al., *Proc. Natl. Acad. Sci. (USA)* 82:3688–3692 (1985); Hwang et al., *Proc. Natl. Acad. Sci. (USA)* 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal therapy.

For parenteral administration, in one embodiment, the composition of the present invention is formulated generally by mixing an effective amount of the active agent at the desired degree of purity, in a unit dosage injectable form (solution, suspension, or emulsion), with an acceptable carrier, i.e., one that is non-toxic to recipients at the dosages and concentrations employed and is compatible with other ingredients of the formulation. For example, the formulation preferably does not include strong oxidizing agents and other compounds that are known to be deleterious to the active agent.

Generally, the formulations are prepared by contacting the active agent uniformly and intimately with liquid carriers or finely divided solid carriers or both. Then, if necessary, the product is shaped into the desired formulation. When the carrier is a parenteral carrier, it is preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrns; chelating agents such as EDTA; sugar alcohols such as mannitol or sorbitol; counterions such as sodium; and/or nonionic surfactants such as polysorbates, poloxamers, or PEG.

The compositions of the present invention are typically formulated in such vehicles at a concentration of active agent of about 1 mg/mL to 240 mg/nL, preferably 30 to 120 mg/mL.

It will be understood that the use of certain of the foregoing excipients, carriers, or stabilizers may result in the formation of salts depending upon the particular substitutent (s) on the active agent.

The compositions of the present invention ordinarily will be stored in unit or multi-dose containers, for example, sealed ampules or vials, as an aqueous solution or as a lyophilized formulation for reconstitution. As an example of a lyophilized formulation, 10-mL vials are filled with 5 mL of sterile-filtered 1% (w/v) aqueous solution, and the resulting mixture is lyophilized. The infusion solution is prepared by reconstituting the lyophilized composition using bacteriostatic Water-for-Injection.

The compositions of the present invention will be formulated and dosed in a fashion consistent with good medical practice, taking into account the clinical condition of the individual patient (especially the side effects of treatment with the active agent), the site of delivery of the composition, the method of administration, the scheduling of administration, and other factors known to practitioners. The"effective amount" of active agent for the purposes of the present invention is determined in view of such considerations. Those skilled in the art can readily determine empirically an appropriate "effective amount" for a particular patient.

The key factor in selecting an appropriate dose is the result obtained, as measured, for example, by increases or decreases in serum insulin levels, serum triglyceride levels, serum cholesterol levels, free and total testosterone levels and/or ovulation and/or progesterone and/or sex hormone binding globulin in the patient. The length of treatment needed to observe changes and the interval following treatment for responses to occur appears to vary depending on the desired effect.

As a general proposition, the total effective amount of active agent administered per dose will be in the range of about 1 mg/kg/day to 1,000 mg/kg/day of mammalian patient body weight, although, as noted above, this will be subject to therapeutic discretion. More preferably, this dose is at least 1 mg/kg/day, and most preferably for humans between about 2 and 20 mg/kg/day.

In a most preferred embodiment, the inventive compositions are formulated for oral delivery according to the methods known to those skilled in the art. For example, the active agent is combined with suitable sweetening agents, flavoring agents, coloring agents and preserving agents, in order to obtain a palatable preparation. Tablets, capsules, powders, granules, and the like for oral administration may contain the active agent in admixture with acceptable additives or excipients. Such forms may be prepared by mixing the active agent(s) with one or more additives and excipients, such as inert diluents, granulating agents, disintegrating agents, binding agents and/or lubricating agents, under suitable conditions.

Acceptable additives and excipients are known to those skilled in the art (see, e.g., *Remington's Pharmaceutical Sciences*, 18th ed., A. Gennaro, ed., Mack Publishing Company, Easton, Pa. (1990)). Illustrative examples of acceptable additives and excipients for oral compositions include, but are not limited to, water, non-fat dry milk, maltodextrin, sugar, corn syrup, sodium caseinate, soy protein isolate, calcium caseinate, potassium citrate, sodium citrate, tricalcium phosphate, magnesium chloride, sodium chloride, lecithin, potassium chloride, choline chloride, ascorbic acid, potassium hydroxide such as calcium carbonate, sodium carbonate, lactose, calcium phosphate, carrageenan, vitamin E, zinc sulfate, ferrous sulfate, niacinamide, biotin, vitamin A, calcium pantothenate, copper gluconate, magnesium sulfate, vitamin K, potassium iodide, folic acid, vitamin D, vanillin, cocoa, polysorbate 80, polysorbate 60, magnesium oxide, riboflavin, pyridoxine hydrochloride, cyanocobalamin, aspartame, thiamine, cellulose, methyl cellulose, hydroxypropyl methylcellulose, alginate, polyoxyelthylene sorbitol monooleate, polyoxyethylene stearate, gum acacia, gum tagacanth, polyvinylpyrrolidone, gelatin, calcium carbonate, calcium phosphate, kaolin, starch, and the like.

When administered orally, the inventive composition preferably contains from about 1 mg to about 1200 mg of active ingredient. In the case of D-chiro-inositol, the inventive composition preferably contains from about 10 mg to about 900 mg of DCI, more preferably about 30 mg to about 600 mg and most preferably about 100 mg to about 300 mg.

A second preferred embodiment of the present invention is directed to compositions and methods for treating mammalian metabolic diseases characterized by hyperinsulinemia, hyperandrogenism, hyperlipidemia and/or anovulation, such as polycystic ovary syndrome (PCOS).

In this embodiment, the inventive composition comprises an effective amount of D-chiro-inositol, or a suitable derivative or metabolite thereof, or a compound containing D-chiro-inositol or a derivative or metabolite thereof, and an acceptable carrier. Preferably, the inventive composition comprises D-chiro-inositol.

The inventive method comprises the step of administering to a mammal in need thereof an effective amount of D-chiro-inositol, or a suitable derivative or metabolite thereof, or a compound containing D-chiro-inositol or a derivative or metabolite thereof. Preferably, the inventive method comprises the step of administering to a mammal an effective amount of D-chiro-inositol.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

All patents and publications referred to herein are expressly incorporated by reference.

EXAMPLES

A clinical study of D-chiro-inositol was performed in obese women diagnosed with Polycystic Ovary Syndrome. Fourteen women received D-chiro-inositol (1200 mg/day) and 15 women received placebo for 6 to 8 weeks. An oral glucose tolerance test was performed at the beginning (prior to study treatment) and at the end of the study. Metabolic parameters were also measured at the beginning and end of the study. Serum progesterone levels were measured weekly throughout the study. Results of the study are summarized below:

Insulin response (area under the concentration curve) to a glucose load was significantly ($P=0.0032$) decreased by 72% in women receiving D-chiro-inositol. :Compared to baseline, the 2 hour post-glucose serum insulin level significantly ($p=0.003$) decreased by 104 $\mu$U/mL (68% reduction) in women receiving D-chiro-inositol, but did not significantly change in women receiving placebo.

13 of the 14 women receiving DCI (93%) ovulated, whereas only 4 out 15 women receiving placebo (27%) ovulated ($p<0.001$).

Total testosterone levels significantly decreased by 39% in women receiving DCI ($p=0.0045$), but did not decrease in women receiving placebo ($p=0.8320$).

Free testosterone levels significantly decreased by 62% in women receiving DCI ($p<0.0001$), but did not decrease in women receiving placebo ($p=0.6102$).

Sex hormone binding globulin levels increased by 90% in women receiving DCI ($p=0.0003$), but did not increase in women receiving placebo ($p=0.5477$).

Triglycerides significantly decreased by 42% in women receiving DCI ($p=0.0012$), but did not decrease in women receiving placebo ($p=0.7775$).

What is claimed is:

1. A method for decreasing the level of free and total testosterone in mammals suffering from metabolic diseases characterized by hyperandrogenism and/or anovulation, said method comprising the step of administering to a mammal an effective amount of D-chiro-inositol.

2. The method according to claim 1, wherein said mammal is a human.

3. The method according to claim 1, wherein said effective amount is between about 1 mg/kg of body weight of said mammal per day and about 1000 mg/kg of body weight of said mammal per day.

4. The method according to claim 1, wherein said effective amount is between about 2 mg/kg of body weight of said mammal per day and about 20 mg/kg of body weight of said mammal per day.

5. A method for treating polycystic ovary syndrome, which comprises the step of administering to a mammal in need thereof an effective amount of D-chiro-inositol.

6. The method according to claim 5, wherein said mammal is a human.

7. The method according to claim 5, wherein said effective amount is between about 1 mg/kg of body weight of said mammal per day and about 1000 mg/kg of body weight of said mammal per day.

8. The method according to claim 5, wherein said effective amount is between about 2 mg/kg of body weight of said mammal per day and about 20 mg/kg of body weight of said mammal per day.

9. A method for improving ovulation in mammals suffering from metabolic diseases characterized by hyperandrogenism and/or anovulation, said method comprising the step of administering to a mammal an effective amount of D-chiro-inositol.

10. The method according to claim 9, wherein said mammal is a human.

11. The method according to claim 9, wherein said effective amount is between about 1 mg/kg of body weight of said mammal per day and about 1000 mg/kg of body weight of said mammal per day.

12. The method according to claim 9, wherein said effective amount is between about 2 mg/kg of body weight of said mammal per day and about 20 mg/kg of body weight of said mammal per day.

13. A method for increasing progesterone levels in mammals suffering from metabolic diseases characterized by hyperandrogenism pad/or anovulation, said method comprising the step of administering to a mammal an effective amount of D-chiro-inositol.

14. The method according to claim 13, wherein said mammal is a human.

15. The method according to claim 13, wherein said effective amount is between about 1 mg/kg of body weight of said mi per day and about 1000 mg/kg of body weight of said mammal per day.

16. The method according to claim 13, wherein said effective amount is between about 2 mg/kg of body weight of said mammal per day and about 20 mg/kg of body weight of said mammal per day.

17. A method for increasing sox hormone binding globulin in mammals suffering from metabolic diseases characterized by hyperandrogenism and/or anovulation, said method comprising the step of administering to a mammal an effective amount of D-chiro-inositol.

18. The method according to claim 17, wherein said mammal is a human.

19. The method according to claim 17, wherein said effective amount is between about 1 mg/kg of body weight of said mammal per day and about 1000 mg/kg of body weight of said mammal per day.

20. The method according to claim 17, wherein said effective amount is between about 2 mg/kg of body weight of said mammal per day and about 20 mg/kg of body weight of said mammal per day.

21. A method for treating menstrual irregularity in s suffering from metabolic diseases characterized by hyperandrogenism and/or anovulation, said method comprising the step of administering to a mammal an effective amount of D-chiro-inositol.

22. The method according to claim 21, wherein said mammal is a human.

23. The method according to claim 21, wherein said effective amount is between about 1 mg/kg of body weight of said mammal per day and about 1000 mg/kg of body weight of said mammal per day.

24. The method according to claim, 21, wherein said effective amount is between about 2 mg/kg of body weight of said mammal per day and about 20 mg/kg of body weight of said mammal per day.

25. A method for treating infertility in mammals suffering from metabolic diseases characterized by hyperandrogenism and/or anovulation, said method comprising the step of administering to a mammal an effective amount of D-chiro-inositol.

26. The method according to claim 25, wherein said mammal is a human.

27. The method according to claim 25, wherein said effective amount is between about 1 mg/kg of body weight of said mammal per day and about 1000 mg/kg of body weight of said mammal per day.

28. The method according to claim 25, wherein said effective amount is between about 2 mg/kg of body weight of said mammal per day and about 20 mg/kg of body weight of said mammal per day.

29. A method for treating hyperandrogenism and/or anovulation associated with polycystic ovary syndrome in mammals, said method comprising the stop of administering to a mammal an effective amount of D-chiro-inositol.

30. The method according to claim 29, wherein said mammal is a human.

31. The method according to claim 29, wherein said effective amount is between about 1 mg/kg of body weight of said mammal per day and about 1000 mg/kg of body weight of said mammal per day.

32. The method according to claim 29, wherein said effective amount is between about 2 mg/kg of body weight of said mammal per day and about 20 mg/kg of body weight of said mammal per day.

33. A method for treating amenorrhea or oligomenorrhea in mammals suffering form metabolic diseases characterized by hyperandrogenism and/or anovulation, said method comprising the step of administering to a mammal an effective amount of D-chiro-inositol.

34. The method according to claim 23, wherein said mammal is a human.

35. The method according to claim 23, wherein said effective amount is between about 1 mg/kg of body weight of said mammal per day and about 1000 mg/kg of body weight of said mammal per day.

36. The method according to claim 23, wherein said effective amount is between about 2 mg/kg of body weight of said mammal per day and about 20 mg/kg of body weight of said mammal per day.

* * * * *